United States Patent
Pechstein

(10) Patent No.: US 9,772,300 B2
(45) Date of Patent: Sep. 26, 2017

(54) INDUCTIVE CONDUCTIVITY SENSOR FOR MEASURING THE SPECIFIC ELECTRICAL CONDUCTIVITY OF A MEDIUM

(71) Applicant: Endress + Hauser Conducta Gesellschaft für Mess—und Regeltechnik mbH + Co. KG, Gerlingen (DE)

(72) Inventor: Torsten Pechstein, Radebeul (DE)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 14/754,899

(22) Filed: Jun. 30, 2015

(65) Prior Publication Data
US 2017/0003237 A1    Jan. 5, 2017

(51) Int. Cl.
| | | |
|---|---|---|
| G01R 27/28 | (2006.01) | |
| G01R 27/08 | (2006.01) | |
| G01N 27/02 | (2006.01) | |
| G01N 27/06 | (2006.01) | |
| G01R 27/26 | (2006.01) | |

(52) U.S. Cl.
CPC ........... *G01N 27/023* (2013.01); *G01N 27/02* (2013.01); *G01N 27/06* (2013.01); *G01R 27/2611* (2013.01)

(58) Field of Classification Search
CPC ...... G01N 27/023; G01N 27/02; G01N 27/04; G01N 27/06; G01R 27/2611
USPC .......................................... 324/654, 693, 439
See application file for complete search history.

(56) References Cited

U.S. PATENT DOCUMENTS

| | | | | |
|---|---|---|---|---|
| 6,414,493 | B1 * | 7/2002 | Rezvani | G01N 27/023 324/442 |
| 8,441,267 | B2 * | 5/2013 | Eberheim | G01N 27/023 324/439 |
| 8,933,709 | B2 * | 1/2015 | Volker | G01R 27/22 324/654 |

* cited by examiner

*Primary Examiner* — Amy He
(74) *Attorney, Agent, or Firm* — Bacon & Thomas, PLLC

(57) ABSTRACT

An inductive conductivity sensor and a method for measuring specific electrical conductivity of a medium, comprising a transmitting coil fed by means of an input signal; coupled with the transmitting coil via the medium; a receiving coil, which delivers an output signal, which is a measure for the conductivity of the medium; and surrounding the transmitting coil and the receiving coil a housing, which has, intended for immersion in the medium, at least one housing section, whose housing wall surrounds the transmitting coil and the receiving coil. The housing section includes at least a first electrically conductive contact intended for contact with the medium and a second electrically conductive contact intended for contact with the medium. The conductivity sensor includes an electrically conductive conductor and the first contact is connected with the second contact via the conductor, wherein the conductor and the electrically conductive contacts are so embodied that they form via an ionic conduction path of the medium a closed electrical current path around the transmitting coil and the receiving coil.

10 Claims, 3 Drawing Sheets

INDUCTIVE CONDUCTIVITY SENSOR FOR MEASURING THE SPECIFIC ELECTRICAL CONDUCTIVITY OF A MEDIUM

TECHNICAL FIELD

The invention relates to an inductive conductivity sensor for measuring the specific electrical conductivity of a medium as well as to a method for measuring the specific electrical conductivity with such a conductivity sensor.

BACKGROUND DISCUSSION

Inductive conductivity sensors serve in a large number of applications in laboratory and process measurements technology for registering the specific electrical conductivity of a liquid medium. They are used preferably where large measuring ranges and high chemical or thermal loadings occur. This is the case, for example, in a large number of industrial, chemical processes, however, also in the case of hot steam sterilization methods, which are frequently applied due to hygienic requirements in the field of foods technology.

An inductive conductivity sensor includes a transmitting coil and a receiving coil, which are, as a rule, embodied as ring coils, also referred to as toroidal coils. A conductivity sensor of such type functions as a kind of double transformer, wherein the transmitting and receiving coils are inserted so far into the medium that a closed electrical current path can form extending through the medium and passing through the transmitting and receiving coils. When the transmitting coil is excited with an alternating voltage signal as an input signal, it produces a magnetic field, which induces in the closed path through the medium passing through the coils an electrical current, whose strength depends on the electrical conductivity of the medium. Since this electrical alternating electrical current in the medium, in turn, brings about a variable magnetic field surrounding it, an alternating electrical current is induced in the receiving coil as an output signal. This alternating electrical current, or a corresponding alternating voltage, delivered from the receiving coil as an output signal is a measure for the electrical conductivity of the medium.

For feeding the transmitting coil with an alternating voltage, an inductive conductivity sensor includes a driver circuit connected with the transmitting coil. For registering the output signal of the receiving coil, the conductivity sensor includes, electrically connected with the receiving coil, a receiving circuit, which is embodied to output the registered measurement signal, in given cases, conditioned by the receiving circuit, to a sensor electronics, which serves further to process the measurement signal and, in given cases, to digitize it. Frequently, conductivity sensors are embodied as measuring probes at least sectionally immersible in the medium. Such a measuring probe includes a housing, in which are accommodated the transmitting and receiving coils, in given cases, the driver circuit and the receiving circuit, as well as other circuit parts assembled with the transmitting and receiving circuits into a sensor circuit. The measuring probe is in such an embodiment connected with a separately situated superordinated unit, for example, a display unit, a measurement transmitter, a computer or a control system. The superordinated unit can be embodied both for supplying energy to the measuring probe as well as also for data communication with the measuring probe. The sensor circuit optionally contained in the measuring probe can be embodied to forward the further processed, in given cases, digitized, measurement signal to the superordinated unit. The corresponding measured value can be displayed via the superordinated unit by means of a display system or output via a data interface.

Inductive conductivity sensors have a lower limit of detection in the region of, for instance, 10-200 µS/cm. Because of this, these sensors are not applicable in the pure and cleanest water fields.

The cause for the lower measuring range limit in the case of inductive conductivity sensors is that the measurement current induced in the analyte in the case of low conductivities is very small and the existing capacitive coupling of the transmitting coil to the receiving coil produces a base signal, which is greater than or equal to the measurement signal. In other words, the signal/noise ratio is not good.

Besides the above described, inductive conductivity sensors, there are also conductive conductivity sensors. In such case, determining the conductivity in the medium occurs with a measuring arrangement, in the case of which, as in the case of a capacitor, two electrodes are located opposite one another. The electrical resistance, or its reciprocal value, the conductance, is measured using Ohm's law. The specific conductivity is ascertained from the conductance using the cell constants determined from the sensor geometry.

In the case of large conductivities, conductive conductivity sensors exhibit polarization phenomena on the electrodes, which contact the analyte. Because of the principles involved, these effects do not occur in the case of inductive conductivity sensors. Therefore, inductive conductivity sensors are applied for high conductivities and conductive conductivity sensors for low conductivities. Today, processes, in which measurements must be made both in the case of very high as well as also very low conductivities, are equipped either with two conductivity sensors, namely an inductive conductivity sensor and a conductive conductivity sensor, or with conductive, four pole sensors. The latter, however, still have a lower upper measuring limit than an inductive conductivity sensor.

SUMMARY OF THE INVENTION

An object of the invention is to provide a conductivity sensor, which possesses the ability to measure in cleanest waters and pure water, and no disturbing polarization effects should occur in the case of high conductivities.

The object is achieved by a conductivity sensor comprising: a transmitting coil fed by means of an input signal; a receiving coil coupled with the transmitting coil via the medium, which delivers an output signal, which is a measure for the conductivity of the medium; and surrounding the transmitting coil and the receiving coil a housing, which has, intended for immersion in the medium, at least one housing section, whose housing wall surrounds the transmitting coil and the receiving coil. The conductivity sensor is characterized in that the housing section includes at least a first electrically conductive contact intended for contact with the medium and a second electrically conductive contact intended for contact with the medium, wherein the conductivity sensor includes an electrically conductive conductor and the first contact is connected with the second contact via the conductor, wherein the conductor and the electrically conductive contacts are so embodied that they form via ionic conduction of the medium a closed electrical current path around the transmitting coil and the receiving coil.

It is, thus, possible also in the case of small conductivities to determine conductivity by means of an inductive conductivity sensor. At the same time, there remains the opportunity to ascertain greater conductivities with the same conductivity sensor. This is achieved by shortening the path length of the electrical current induced in the medium, whereby the measurement current is increased and, thus, the measuring range expanded.

In a preferred embodiment, the first contact and the second contact are metal contacts, and the conductor is a metal conductor.

In an advantageous further development, the first and second contacts are manufactured using thin-film technology. In a variant, the first and second contacts are located on the surface of the housing section intended for immersion in the medium. The contacts can, thus, also be placed later.

In order to avoid penetration of water, the first and second contacts are sealed from the interior of the housing.

In an advantageous embodiment, the first and second contacts are led into the interior of the housing, and the conductor is led at least sectionally in the housing.

Alternatively, the first and second contacts are led outside of the housing, and the conductor is led at least sectionally outside of the housing.

In a preferred form of embodiment, the conductor is so embodied that it is led, especially wound, multiply around the transmitting coil or the receiving coil or the transmitting coil and the receiving coil. In this way, the resulting measurement current can be increased by a multiple.

In an advantageous embodiment, the conductor includes at least one switch, which opens and closes the electrical current path. The resulting expanded measuring range can, thus, depending on need, i.e., depending on conductivity, be switched on or off.

In such case, the switch switches-in individual sections, especially windings, of the conductor, depending on conductivity. In the case of low conductivity, thus more windings are connected than in the case of increased conductivity.

The object is further achieved by a method involving a conductivity sensor such as above described, wherein the method comprises steps as follows: transmitting the input signal from the transmitting coil into the medium; converting the output signal of the receiving coil into a value for the conductivity; and switching the conductor in for lessening the effective path length of the induced electrical current in the medium, when the conductivity value subceeds a certain value.

BRIEF DESCRIPTION OF THE DRAWINGS

The invention will now be explained in greater detail based on the drawing, the figures of which show as follows.

DETAILED DISCUSSION IN CONJUNCTION WITH THE DRAWINGS

Figure 1:
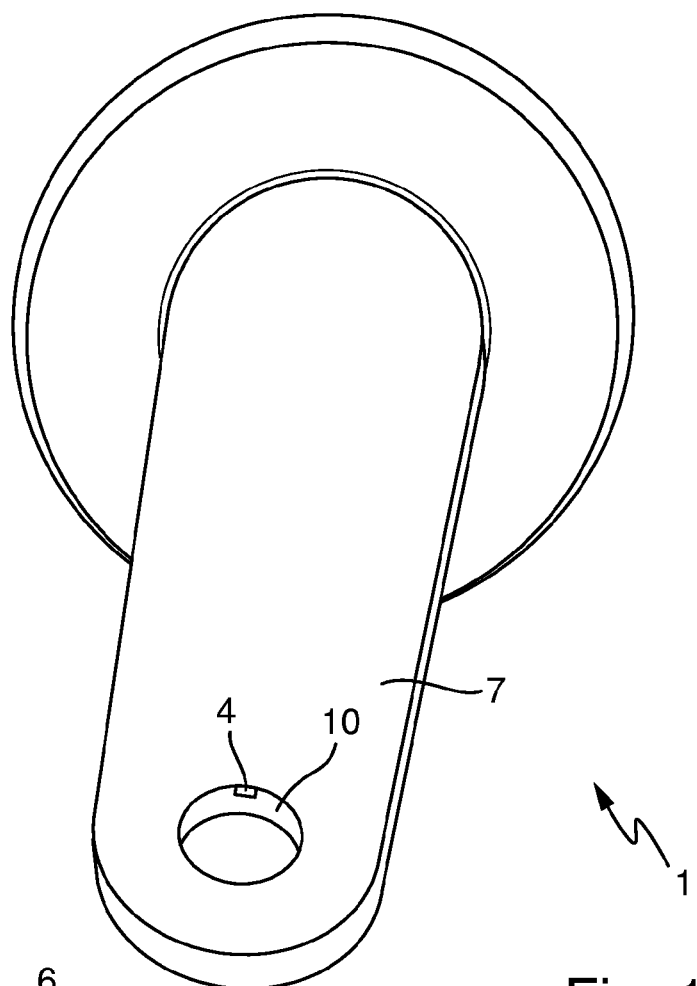
FIG. 1 is a conductivity sensor of the invention in a three dimensional representation.

In the figures, equal features are provided with equal reference characters.

Figure 2:
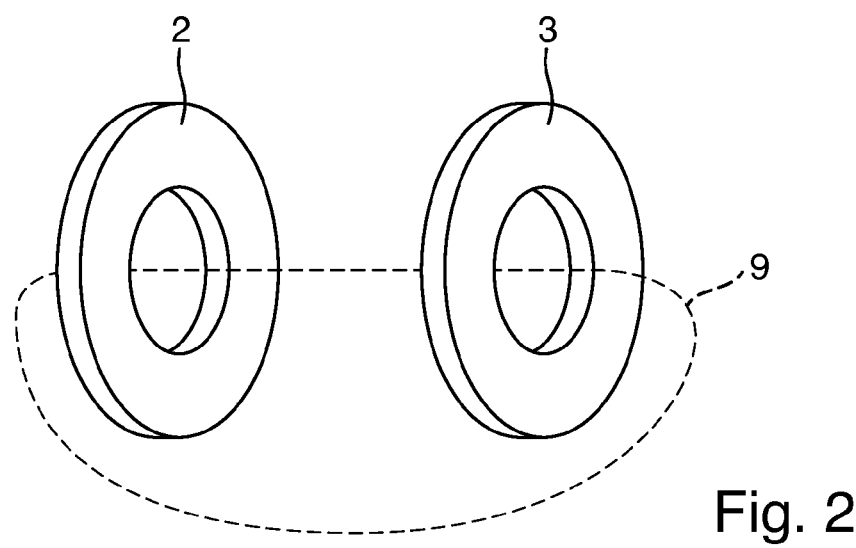
FIG. 2 is a transmitting coil and the receiving coil of a conductivity sensor.
Figure 3:
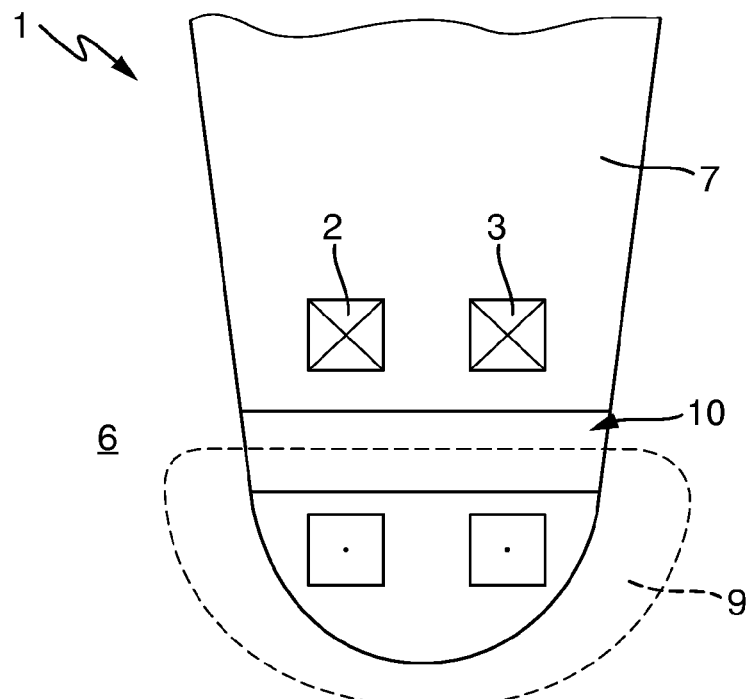
FIG. 3 is a conductivity sensor in cross section.

The conductivity sensor of the invention in its totality is given the reference character 1 and is shown in FIG. 1. First, the measuring principle of a conductivity sensor will be shortly explored based on FIG. 1, FIG. 2 and FIG. 3.

The mentioned figures show a sensor module of an inductive conductivity sensor 1 having a transmitting coil 2 and a receiving coil 3, which are accommodated in a housing 7. The transmitting coil 2 and the receiving coil 3 are arranged opposite one another on sides of a circuit card (not shown) facing away from one another. The transmitting and receiving coils 2, respectively 3, embodied as rotationally symmetric, toroidal coils ("toroids") are, in this way, arranged coaxially behind one another. The circuit card includes conductive traces contacting the coils, which connect the transmitting coil 2 with a driver circuit and the receiving coil 3 with a receiving circuit. The driver circuit and the receiving circuit can be components of a sensor circuit arranged on the circuit card.

The housing 7 has a duct 10 passing through the transmitting coil 2 and the receiving coil 3 along their axis of rotation. If housing 7 is immersed in an electrically conductive medium 6, such surrounds the housing 7 and penetrates into the duct 10, so that a closed electrical current path 9 can form in the medium passing through the two coils 2, 3, when the transmitting coil 2 is excited with an input signal, thus an alternating voltage.

The conductivity sensor functions as a type of double transformer, wherein the transmitting and receiving coils 2, 3 are inserted, such as mentioned, sufficiently far into the medium 6 that a closed electrical current path 9 extending through the medium 6 can form passing through the transmitting and receiving coils 2, 3. When the transmitting coil 2 is excited with an alternating voltage signal as input signal, a magnetic field is produced, which induces an electrical current 9 passing through the coils 2, respectively 3, whose strength depends on the electrical conductivity of the medium 6. There results, thus, an electrical current path with ionic conduction in the medium 6. Since this alternating electrical current brings about in the medium, in turn, a variable magnetic field surrounding it, an alternating electrical current is induced in the receiving coil 3 as output signal. This alternating electrical current, respectively a corresponding alternating voltage, delivered by the receiving coil 3 as output signal is a measure for the electrical conductivity of the medium 6.

The size of the induced measuring electrical current depends, however, also on the path length through the medium. By shortening the path length 9 of the electrical current induced in the medium, the measurement current can be increased and the measuring range expanded.

Figure 4:
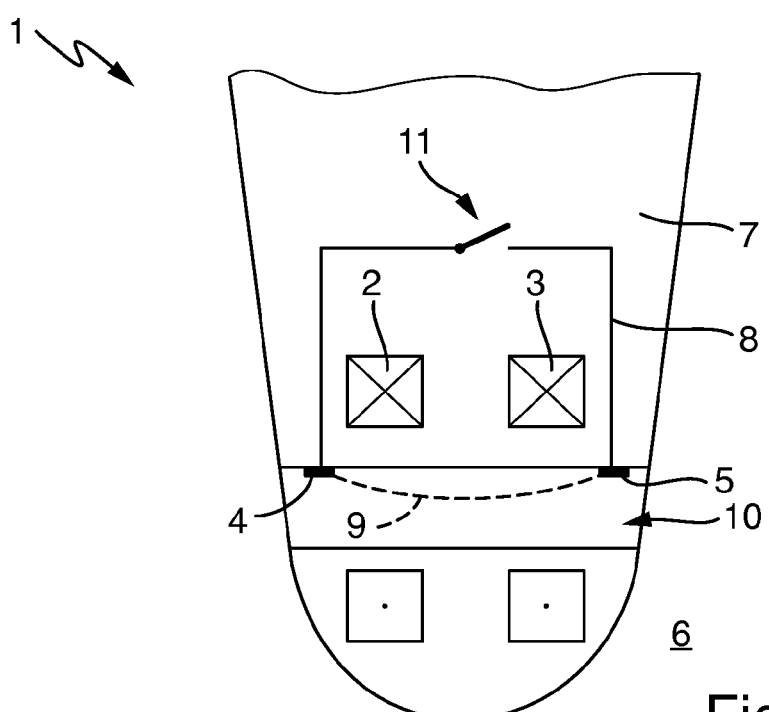
FIG. 4 is a conductivity sensor of the invention in cross section.

FIG. 4 shows an example of an embodiment. Mounted for contact with the medium 6 are a first electrically conductive contact 4 and a second electrically conductive contact 5. The electrically conductive contacts 4, 5 are preferably metal contacts. In an embodiment, the contacts 4, 5 are sealed from the housing interior.

The contacts 4, 5 are connected in the housing interior with a conductor 8, which produces a closed electrical current path around the transmitting and receiving coils 2, 3. In an embodiment, the conductor 8 is a metal conductor.

The contacts 4, 5 and the conductor 8 form via an ionic conduction path 9 in the medium 6 a closed electrical current path around the transmitting coil 2 and the receiving coil 3. In a form of embodiment, conductor 8 is wound around the transmitting and receiving coils 2, 3.

In the case of high conductivities of a medium, this measure is not required and can be interrupted by a switch 11. In the case of small conductivities of a medium, the switch 11 can be closed, which increases the measurement current and expands the lower measuring range limit to lower conductivities. The switching-in of the conductor 8 for lessening the effective path length of the induced electrical current in the medium 6 is done when the value of the conductivity subceeds a certain value, e.g. a value of, for instance, 100 µS/cm.

Figure 5:
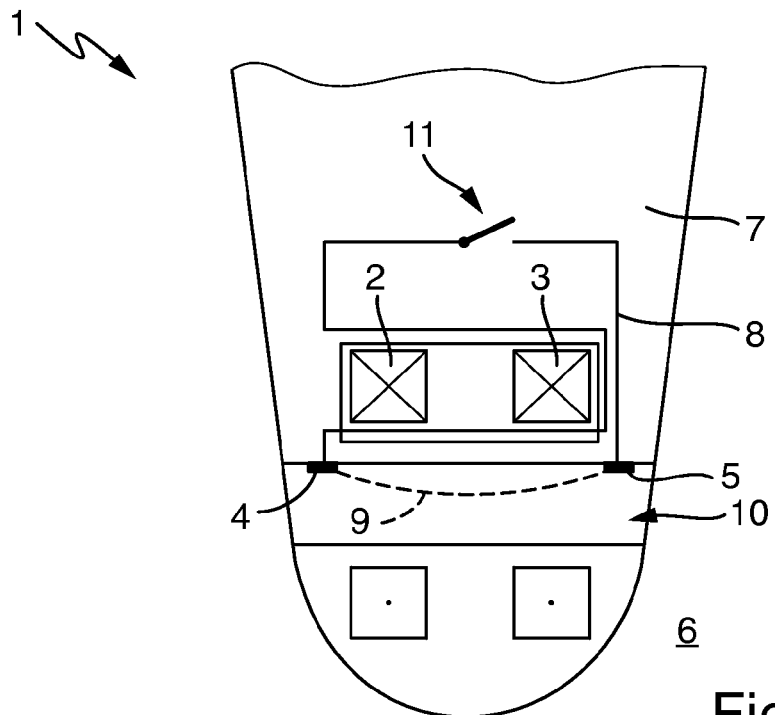
FIG. 5 is a conductivity sensor of the invention in cross section in one embodiment.

FIG. 5 shows another form of embodiment. In such case, the housing-internal conductor 8 is led multiple times, for instance, two times, three times, or, in general, N-times, around the transmitting or receiving coil 2, 3. In this way, the measurement current is increased multiple times, for instance, to a value twice, thrice, or, in general, N-times as much. In a form of embodiment, the conductor 8 is wound multiple times, for instance, two times, three times, or, in general, N-times, around the transmitting and receiving coils 2, 3. The conductor 8 can, thus, be led, respectively, multiple times around the transmitting coil 2 or the receiving coil 3 or the transmitting coil 2 and the receiving coil 3.

Figure 6:
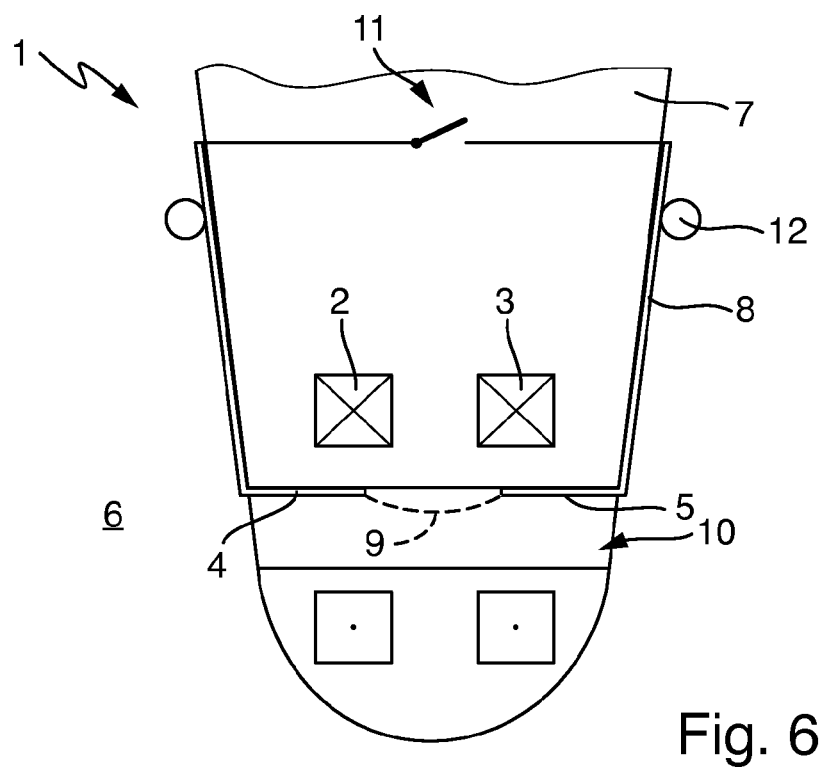
FIG. 6 is a conductivity sensor of the invention in cross section in an additional embodiment.

In an additional form of embodiment, which is shown in FIG. 6, the contacts 2, 3 are applied with thin layer technology on the surface of the housing, and, via a process seal 12, contacted outside of the medium to the housing interior. These contacts are placed, for instance, on the surface of the housing section intended for immersion in the medium.

In an embodiment, the conductor 8 can, both in the case of the cable variant as well as also in the case of the thin layer variant, be led at least sectionally outside of the housing 7.

The invention claimed is:

1. An inductive conductivity sensor for measuring specific electrical conductivity of a medium, comprising:
    a transmitting coil provided with an input signal;
    a receiving coil coupled with said transmitting coil via the medium and configured to generate an output signal that is a measure for the conductivity of the medium;
    a housing surrounding said transmitting coil and said receiving coil, the housing including at least one housing section for immersion in the medium having a housing wall that surrounds said transmitting coil and said receiving coil, said housing section including a first electrically conductive contact for contacting the medium and a second electrically conductive contact for contacting the medium; and
    an electrically conductive conductor, wherein said first electrically conductive contact of said housing section is connected with said second electrically conductive contact of said housing section via said conductor,
    wherein said electrically conductive conductor and said first and second electrically conductive contacts form, via an ionic conduction path of the medium, a closed electrical current path surrounding said transmitting coil and said receiving coil, and said electrically conductive conductor includes at least one switch that opens and closes the electrical current path to switch a resulting expanded measuring range on or off.

2. The inductive conductivity sensor as claimed in claim 1, wherein:
    said first contact and said second contact are metal contacts and said electrically conductive conductor is a metal conductor.

3. The inductive conductivity sensor as claimed in claim 1, wherein:
    said first contact and said second contact are manufactured using thin layer technology.

4. The inductive conductivity sensor as claimed in claim 3, wherein:
    said first contact and said second contact are located on a surface of said housing section structured for immersion in the medium.

5. The inductive conductivity sensor as claimed in claim 1, wherein:
    said first contact and said second contact are sealed from an interior of said housing.

6. The inductive conductivity sensor as claimed in claim 5, wherein:
    said first contact and said second contact are led into the interior of said housing, and said electrically conductive conductor is led at least partially into said housing.

7. The inductive conductivity sensor as claimed in claim 1, wherein:
    said first contact and said second contact are led outside of the housing, and said electrically conductive conductor is led at least partially outside of said housing.

8. The inductive conductivity sensor as claimed in claim 1, wherein:
    said electrically conductive conductor is so embodied that it is wound around said transmitting coil or said receiving coil.

9. The inductive conductivity sensor as claimed in claim 1, wherein:
    said switch switches-in individual sections, especially windings, of said electrically conductive conductor.

10. A method for measuring specific electrical conductivity of a medium with an inductive conductivity sensor, comprising:
    providing a transmitting coil fed by an input signal; a receiving coil coupled with said transmitting coil via the medium and configured to generate an output signal that is a measure for the conductivity of the medium; a housing surrounding said transmitting coil and said receiving coil, the housing including at least one housing section for immersion in the medium having a housing wall that surrounds said transmitting coil and said receiving coil, said housing section including a first electrically conductive contact for contacting the medium and a second electrically conductive contact for contacting the medium; and an electrically conductive conductor, wherein the first electrically conductive contact of said housing section is connected with said second electrically conductive contact of said housing section via said conductor, wherein said electrically conductive conductor and said first and second electrically conductive contacts form, via an ionic conduction path of the medium, a closed electrical current path surrounding said transmitting coil and said receiving coil, and said electrically conductive conductor includes at least one switch that opens and closes the electrical current path to switch a resulting expanded measuring range on or off, the method comprising:
    transmitting the input signal from the transmitting coil of the inductive conductivity sensor into the medium;
    converting the output signal of the receiving coil into a value for the conductivity; and
    connecting the conductor for lessening the effective path length of the induced electrical current in the medium when the conductivity value falls below a certain value.

* * * * *